United States Patent [19]

Sherrill

[11] 4,390,539

[45] Jun. 28, 1983

[54] METHOD FOR THE TREATMENT OF VIRAL SKIN DISEASES

[75] Inventor: George F. Sherrill, 405-39th St., Newport Beach, Calif. 92663

[73] Assignees: George F. and Irene Sherrill 1978 Trust No. 1, Newport Beach, Calif.; George F. and Irene Sherrill 1978 Trust No. 2, Newport Beach, Calif.; a part interest to each

[21] Appl. No.: 230,545

[22] Filed: Feb. 2, 1981

Related U.S. Application Data

[60] Division of Ser. No. 29,698, Apr. 13, 1979, Pat. No. 4,267,007, which is a continuation of Ser. No. 781,170, Mar. 25, 1977, abandoned.

[51] Int. Cl.$^3$ .................. A61K 31/505; A61K 31/44; A61K 31/40; A61K 31/14
[52] U.S. Cl. .................................. 424/251; 424/263; 424/274; 424/329
[58] Field of Search ...................... 424/251, 274, 263

[56] References Cited

FOREIGN PATENT DOCUMENTS 809655  2/1959  United Kingdom .

OTHER PUBLICATIONS

Chemical Abstracts 82:26890h, (1975).
Physicians' Desk Reference, 27 ed., 1973, p. 699.
Technical Bulletin No. 91, R. T. Vanderbilt Co., 30 Winfield St., Norwalk, Conn. 06855, Title Vancide, 89RE, published 1971.

Primary Examiner—Jerome D. Goldberg
Attorney, Agent, or Firm—Lyon & Lyon

[57] ABSTRACT

There is disclosed an improved method for the treatment of viral skin diseases comprising the topical application of a chemical composition to the infected areas wherein the composition comprises captan and a surface active bactericide. In its preferred embodiment, the bactericide comprises benzethonium chloride. The composition is preferably incorporated into a topical vehicle to facilitate its application to the infected areas.

18 Claims, No Drawings

METHOD FOR THE TREATMENT OF VIRAL SKIN DISEASES

This is a division of application Ser. No. 029,698, filed Apr. 13, 1979, now U.S. Pat. No. 4,267,007, which application is a continuation of application Ser. No. 781,170, filed Mar. 25, 1977, now abandoned.

BACKGROUND OF THE INVENTION

The present invention relates to the method of treating viral skin disorders and in particular relates to the method for treating herpes zoster.

Herpes zoster, which is commonly known as shingles, is a viral disease which frequently causes excruciating, prolonged pain and discomfort. A typical shingles patient suffers a great amount of pain for a period of six weeks to six months. Further, other symptoms of the disease may continue for a year or longer and in some cases even for the rest of the patient's life. Blindness, neuritis, and partial paralysis are some of the severe disabilities which can result from the disease. One particularly bad characteristic of the ailment is that it tends to recur periodically, particularly in older patients.

To describe the disease in technical terms, the virus attacks one or more sensory ganglia, usually on one side of the body but sometimes on both. The inflammatory process can extend inward to the meninges and into the root entry zone of the spinal cord; occasionally it involves the ventral horns, resulting in lower motor neuron paralysis of more or less segmental distribution. The related peripheral nerve or nerves are involved by a true inflammatory neuritis. Encephalitis and myelitis occasionally occur in debilitated patients.

The earliest symptom is pain in the distribution of the affected root or roots around the trunk, or as a linear strip on the upper or lower limb, or in one or more divisions of the trigeminal nerve. It involves the pinna, external auditory meatus, and anterior pillar of the fauces in geniculate herpes. In rare instances the disease is painless. However, in most cases, the skin of the infected zone is hypersensitive even before the rash appears. In some cases muscular paralysis may appear within one or two weeks after the rash has appeared. Such paralysis is uncommon except in the case of geniculate herpes, which is usually accompanied by facial paralysis resembling Bell's palsy.

Postherpetic neuralgia is a common sequel, particularly in patients over fifty. The pain is persistent, and is usually aggravated by emotion and fatigue. Initially, the skin is sensitive to touch, but after a year or two this sensitivity disappears.

In ophthalmic herpes there is special danger to the eye, which may in some cases have a secondary bacterial infection. This secondary infection can lead to panophthalmitis. Further, corneal opacities or glaucoma can also result from the herpes.

In most cases, herpes zoster occurs in otherwise healthy individuals. However, in a minority of cases, it occurs in a background of lymphoma, leukemia, carcinoma, radiation therapy, or the use of immunosuppressive drugs.

Prior methods of treatment of viral skin diseases such as shingles include the use of cortisone, steroids, anesthetics, etc. However, prior methods of treatment have been generally unsuccessful. Therefore, an effective method for the treatment of viral skin diseases is still desired.

SUMMARY OF THE INVENTION

It is therefore an object of the present invention to provide an improved method for the treatment of viral skin diseases.

This and other objects and advantages are obtained by topically applying a chemical composition to the infected areas wherein the composition comprises captan and a surface active bactericide. In its preferred embodiment, the bactericide comprises benzethonium chloride. The composition is preferably incorporated into a topical vehicle to facilitate its application to the infected areas. The application of the composition to the infected areas, in many cases results in partial or complete remission of the disease.

A more thorough disclosure of the objects and advantages of the present invention is presented in the detailed description which follows.

DETAILED DESCRIPTION OF THE INVENTION

The present invention contemplates an improved method for the treatment of viral skin diseases such as shingles, herpes simplex I and II and warts comprising the application of a chemical composition to the infected areas wherein the composition comprises captan and a surface active bactericide. In its preferred embodiment, the composition comprises captan and benzethonium chloride. The composition is preferably incorporated into a topical vehicle to facilitate its application to the infected areas.

Captan is a known fungicide and bactericide and has the formula N-(trichloromethylthio)-4-cyclohexene-1,2-dicarboximide. Suitable surface active bactericides for the practice of the present invention are quaternary ammonium salts such as: cetyl pyridinium chloride, benzalkonium chloride, benzethonium chloride, methylbenzethonium chloride, thonzonium bromide, triclobisonium and domiphen bromide. However, it will be obvious to one skilled in the art that other types of surface active bactericides may also be utilized in combination with captan in the practice of the present invention.

The composition is preferably incorporated into a topical vehicle to facilitate its application to the infected areas. The topical vehicle functions to dilute the active ingredient and also functions to assist in the absorption of the active ingredients into the skin. Preferably, the vehicle is capable of dissolving substantial amounts of both the captan and the surface active bactericide to form a topical preparation. Suitable vehicles are absorbent, emulsion and oleaginous ointment bases such as hydrophilic petrolatum, anhydrous lanolin, lanolin, hydrophilic ointment, cold cream, petrolatum, propylene glycol, polyoxyl stearate, glycol ethers and derivatives, cetyl and stearyl alcohol, stearic acid, mineral oils, caster oil, glycerin, polyethylene glycol, animal oil and vegetable oils such as olive oil, corn oil, peanut oil and cocoa butter. Other suitable vehicles are Brij 30 and Brij 35. (Brij is a trademark which was registered by the Atlas Powder Company, Wilmington, Del. The product is described in *The Merk Index*, 9th Ed. (1976) at Page 177, Paragraph 1377, and is a series of polyoxyethylene ethers of fatty alcohols which include derivatives of detyl, stearyl and oleyl alcohols, each ethoxylated with 2, 10, or 20 moles of ethylene oxide, and of lauryl alcohol, ethoxylated with 4 or 23 moles of ethylene oxide.) Combinations of one or more of the above vehicles may also be utilized in the practice of the present invention. However, it will be obvious to one skilled in the art that other suitable topical vehicles may also be utilized in the practice of the present invention.

It will be obvious to one skilled in the art that the topical vehicle may also comprise, in addition to bodying agents, humectants, saponifying agents, emulsifiers, solvents penetrants, pH regulators, plasticizers, emollients, preservatives, hardening agents, pigments and perfumes.

In the practice of the present invention, it is preferred that the topical preparation further comprise a stabilizer to prevent decomposition of the active ingredients. Suitable stabilizers for the practice of the present invention are butylated hydroxytoluene (BHT) and tocopherol. However, it will be obvious to the art skilled that other suitable stabilizers may also be utilized in the practice of the present invention.

The topical preparation preferably contains an effective amount of captan, e.g., from about 10% by weight to about 0.01% by weight, preferably about 1% by weight and an effective amount of the surface active bactericide, e.g., from about 3% to about 0.01% by weight, preferably 0.1% by weight. The preparation further preferably contains an effective amount of stabilizer, e.g., from about 0.5% by weight to about 0.005% by weight, preferably about 0.02% by weight. In this regard, it should be noted that increasing the concentration of the captan and the surface active bactericide in the preparation can cause irritation of the skin and in some cases, allergic reactions. Thus, it is preferred that a minimum amount of both compounds which enables effective action and avoids allergic reaction be incorporated into the preparation. However, it will be obvious to one skilled in the art that for more recalcitrant conditions, it may be desired to increase the amount of the active ingredients in the preparation to enable effective action. Suitable topical preparation for the practice of the present invention are as follows:

| I. Captan | 1.00%* | III. Captan | 5.00% |
|---|---|---|---|
| Benzethonium Chloride | 0.10 | Benzethonium Chloride | 0.40 |
| BHT | 0.02 | BHT | 0.02 |
| Brij 30 | 10.00 | Corn Oil | 30.00 |
| Brij 35 | 10.00 | Petrolatum | 64.58 |
| Cetyl Alcohol | 10.00 | | 100.00% |
| Petrolatum | 68.88 | | |
| | 100.00% | | |
| II. Captan | 3.00% | IV. Captan | 1.00% |
| Benzethonium Chloride | 0.03 | Benzethonium Chloride | 0.10 |
| BHT | 0.02 | BHT | 0.02 |
| Caster Oil | 10.00 | Brij 30 | 7.50 |
| Brij 35 | 10.00 | Brij 35 | 7.50 |
| Cetyl Alcohol | 10.00 | Cetyl Alcohol | 7.50 |
| Petrolatum | 66.68 | Caster Oil | 7.50 |
| | 100.00% | Petrolatum | 68.88 |
| | | | 100.00% |

*All percentages by weight

The topical composition is preferably spread thinly over the infected areas of the skin. The composition is preferably applied to the infected areas once or twice a day until all of the symptoms disappear. In the treatment of shingles, upon the application of the agent to the infected areas, the pain is usually alleviated in a matter of seconds or minutes and the lesions and rashes begin to heal. With the palliation of pain, the patient can usually sleep comfortably, wear conventional clothes and lead a generally normal life. Eventually, the treatment results in remission of the lesions and rashes.

In the treatment of shingles and herpes simplex I and II the present method is most effective when the topical agent is applied during the early, active stages of the disease. Thus, in the treatment of shingles, the topical agent is preferably applied to the infected areas during the first six weeks following the onset of the symptoms of shingles. When the agent is applied more than six weeks, and more particularly, more than two months after onset of the symptoms of shingles, in some cases, the application of the agent does not result in palliation. It is believed that this is because the disease has by that time run its course and there only remains the aftereffects of the disease.

Although the rational for the successful results of the present method are not fully understood, it is believed that the captan and the surface active bactericide cooperate synergistically to form a combination which enables an effective action against viral skin diseases. In the treatment of shingles, this effect is obtained even though neither ingredient is analgesic or anesthetic.

The composition of the present invention has been tested on several patients suffering from shingles. In each case a diagnosis of shingles was made by a medical doctor. In all cases a topical agent corresponding to that of Example I was applied topically to the infected areas of the skin. However, in some cases the preparation contained no stabilizer (BHT) and in those cases the percentage of petrolatum ws 68.90. The topical preparation was prepared by combining the three alcohols (brij 30, brij 35 and cetyl) and the petrolatum in a vessel, and then gradually raising the temperature to about 125° F. to melt the alcohols and the petrolatum. Purified captan, benzethonium chloride and BHT were then added to the melt with stirring and dissolved in the alcohols. The melt was then cooled with stirring to produce a homogeneous mass of ointment having the general appearance and consistency of petrolatum.

The following are case histories of the treatment of these patients. It is to be understood that these histories are given by way of illustration and not of limitation.

Case History No. I

A white female developed herpes zoster of the cervical plexus of her neck. Five days after the onset of the ailment, the topical preparation of the present invention was applied to the infected areas. On the day following application of the ointment the pain disappeared and the lesions began to dry out. Her only remaining symptom was a slight itching. All symptoms had disappeared within eleven days after onset of the disease.

Case History No. II

A white female developed herpes zoster while hospitalized for treatment of bleeding gastric ulcers. The infected area was on her right side, adjacent the 4-5 lumbar vertebrae. The symptom of the disease was a small area of blisters which gradually extended toward the right, in a band about two inches wide and seven inches long. She experienced severe itching, burning and pain. Application of the topical preparation of the present invention gave immediate relief from pain and the eruption disappeared without about one week after application.

Case History No. III

A white adult female developed severe pain during a particular day, and by that night the skin on her buttocks and the back of her thighs was very sore and there were spots on her left side. She was unable to sit down with comfort. The topical preparation of the present invention was applied to the infected areas and it substantially alleviated the pain. Three days later she returned to the doctor who had originally diagnosed the ailment as shingles and the doctor found her condition much improved.

Case History No. IV

A white adult female had suffered from shingles over a period of several years and in some years it had recurred several times during the year. No previous remedy had offered any relief. The topical preparation of the present invention was applied to the infected areas and the itching and the burning pain promptly diminished to the point where the patient felt comfortable. She maintained the areas "moist" with a preparation, which seemed to shorten the distress period. The disease has subsequently recurred periodically, but less frequently than prior to the first application of the preparation of the present invention.

Case History No. V

A white adult female suffered from itching and knifing pains, and had a rash four to five inches wide on each side of her breasts. The case was diagnosed by a doctor as a well segmented case of shingles which would be expected to last about six weeks to six months. The topical preparation of the present invention was applied two days after onset of the itching and pains and the first application relieved both itching and pains. With additional applications the rash completely disappeared in approximately two weeks after onset of the ailment.

Case History No. VI

An adult male had red blotches on the neck and chest and itching and burning sensations. Five days later, while still in discomfort, the patient applied the topical preparation of the present invention and achieved prompt relief. No discomfort recurred after application of the preparation.

Case History No. VII

An adult female experienced a case of shingles which exhibited symptoms of extreme pain in the upper portion of the left side of her back and extended approximately half way around to her front at the waistline. After a few days of pain, the patient broke out around the waist with a painful rash similar to chicken pox eruptions. The topical preparation of the present invention was applied, and it gave immediate great relief. There was no extension of the rash in contrast with an earlier experience with shingles wherein the rash had extended to both sides of the patient.

Case History No. VIII

An adult female who was suffering from shingles was unable to lay down in bed for five days due to the pain. Application of the topical preparation of the present invention to the infected areas achieved prompt relief from the pain. The patient was subsequently able to nightly enjoy several hours of sleep.

Case History No. IX

An adult female who was suffering severe pain from shingles achieved relief within moments after the application of the topical preparation of the present invention. Although other preparations had previously been applied, none had alleviated the unbearable pain.

Case History No. X

An adult female applied the topical preparation of the present invention to the infected regions after two weeks of suffering from shingles. Minutes after the application, the pain ceased and inflammation of the sores commenced to diminish.

Case History No. XI

An adult female applied the topical preparation of the present invention to blisters of shingles which had formed on her face. Several applications were made to each blister which resulted in healing the blisters.

Case History No. XII

An adult female suffered extreme discomfort, with related loss of sleep and nervous tension, caused by unrelieved symptoms. Other ointments had been used without success. The topical preparation of the present invention was applied about three months after onset of the disease and it provided immediate relief. Thereafter, for a period of about a year and a half, the residual symptoms were kept under control by repeated applications of the preparation.

Case History No. XIII

An adult female suffering from shingles exhibited symptoms of swelling in one eye, so that the eye was almost swollen shut. The topical preparation of the present invention was applied to the eye-lid and surrounding area. Immediately, all progress of the disease was arrested and eventually with repeated application remission of the disease occurred.

Case History No. XIV

An adult female with facial herpes zoster applied the topical preparation of the present invention after scabs had formed. The preparation softened the scabs and relieved all sensitivity in the area.

While an embodiment and application of this invention has been shown and described, it will be apparent to those skilled in the art that many more modifications are possible without departing from the inventive concepts herein described. The invention, therefore, it not to be restricted except as is necessary by the prior art and by the spirit of the appended claims.

I claim:

1. A method for the treatment in humans of viral skin diseases susceptible to topical treatment comprising the topical application to infected areas of a person of an amount of a composition effective to treat said viral skin diseases wherein the composition comprises an effective amount of at least 0.1% captan and an effective amount of surface active quaternary ammonimum salt salt bactericide.

2. The method of claim 1 wherein said quaternary ammonium salt is selected from the group consisting of cetyl pyridinium chloride, and thonzonium bromide.

3. The method of claim 1 wherein said composition is combined with a topical vehicle to form a topical preparation.

4. The method of claim 3 wherein said vehicle is selected from the group consisting of absorbent, emulsion and oleaginous ointment bases.

5. The method of claim 3 wherein said captan comprises about 0.01% to about 10.0% by weight of said preparation.

6. The method of claim 3 wherein said surface active bactericide comprises from about 0.01% to about 3.0% by weight of said preparation.

7. The method of claim 3 wherein said preparation further comprises an effective amount of a stabilizer.

8. The method of claim 7 wherein said stabilizer is selected from the group consisting of butylated hydroxytoluene and tocopherol.

9. The method of claim 7 wherein said stabilizer comprises from about 0.005 percent to about 0.5 percent by weight of said preparation.

10. A method for the treatment in humans of viral infections of herpes simplex I, herpes simplex II or herpes zoster comprising the topical application to infected areas of a person of an amount of a composition effective to treat said viral infection wherein the composition comprises an effective amount of at least 0.1% captan and an effective amount of surface active quaternary ammonium salt bactericide.

11. The method of claim 10 wherein said quaternary ammonium salt is selected from the group consisting of cetyl pyridinium chloride, and thonzonium bromide.

12. The method of claim 10 wherein said composition is combined with a topical vehicle to form a topical preparation.

13. The method of claim 12 wherein said vehicle is selected from the group consisting of absorbent, emulsion and oleaginous ointment bases.

14. The method of claim 12 wherein said captan comprises about 0.01% to about 10.0% by weight of said preparation.

15. The method of claim 12 wherein said surface active bactericide comprises from about 0.01% to about 3.0% by weight of said preparation.

16. The method of claim 12 wherein said preparation further comprises a stabilizer.

17. The method of claim 16 wherein said stabilizer is selected from the group consisting of butylated hydroxytoluene and tocopherol.

18. The method of claim 16 wherein said stabilizer comprises from about 0.005% to about 0.5% by weight of said preparation.

* * * * *